United States Patent [19]

Ward

[11] 4,338,953

[45] Jul. 13, 1982

[54] BREAST MEASURING APPARATUS

[76] Inventor: Christopher M. Ward, 44, Wensleydale Rd., Hampton, Middlesex, England

[21] Appl. No.: 220,253

[22] Filed: Dec. 24, 1980

[30] Foreign Application Priority Data

Dec. 28, 1979 [GB] United Kingdom ............... 7944551

[51] Int. Cl.³ .............................................. A61S 5/10
[52] U.S. Cl. .................................. 128/774; 33/174 D; 128/505
[58] Field of Search ............... 128/725, 727, 462, 505, 128/774; 33/174 D

[56] References Cited

U.S. PATENT DOCUMENTS

| 1,119,047 | 12/1914 | Simmons | 128/462 |
| 2,559,501 | 7/1951 | Graf | 33/174 D |
| 2,842,775 | 7/1958 | Pangman | 128/462 |
| 3,635,214 | 7/1970 | Rand et al. | 128/727 |
| 3,720,202 | 3/1973 | Cleary | 128/727 |
| 3,862,628 | 1/1975 | Williams | 128/727 |
| 3,871,364 | 3/1975 | Boehringer | 128/727 |
| 3,883,902 | 5/1975 | Lynch | 128/462 |
| 4,024,856 | 5/1977 | Kirianoff | 128/774 |

Primary Examiner—Kyle L. Howell
Assistant Examiner—Nancy A. B. Swisher
Attorney, Agent, or Firm—Cushman, Darby & Cushman

[57] ABSTRACT

Apparatus for use in estimating the volume of a human breast includes a cup which substantially covers the breast and is lined with a flexible membrane, the membrane defining a space within the cup and the space being coupled to a fluid container having means to vary the volume of fluid within the container, and for indicating changes in the volume of fluid within the container, whereby variations in volume of fluid in the said space result in corresponding variations in volume of fluid within the container.

6 Claims, 1 Drawing Figure

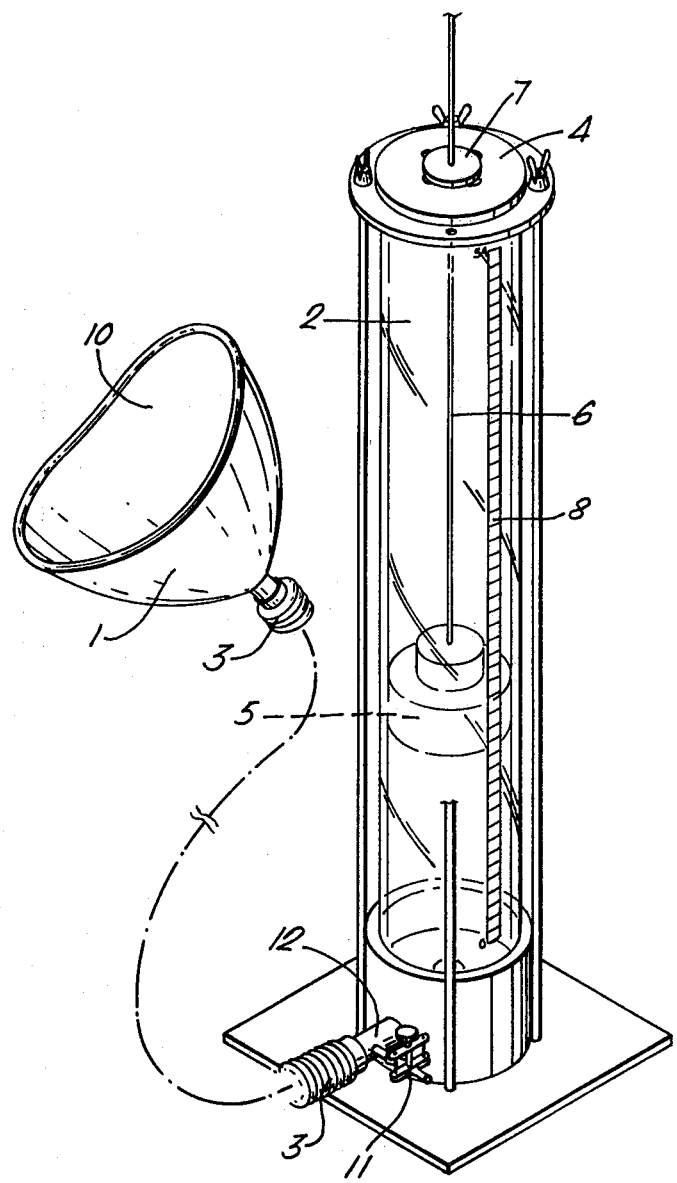

BREAST MEASURING APPARATUS

This invention relates to apparatus for use in estimating the volume of the human breast.

In the course of surgery aimed to create symmetry between a pair of human breasts, it is necessary to establish with a reasonable degree of accuracy, the volume of the breasts. Methods previously proposed have not been entirely successful. Such previously proposed methods included taking measurements with a tape measure. The apparatus and method proposed by the present invention enable the volume of a human breast to be determined comparatively accurately.

In a preferred embodiment, the apparatus includes a cup, a flaccid membrane lining the inside of the cup and means to detect the volume change between the membrane and the cup when the membrane is pressed against a breast.

An embodiment of the invention will now be described, by way of example, with reference to the single FIGURE of the accompanying drawing, which shows a perspective view of the apparatus.

Referring to the drawing, there is shown a cup 1, a cylinder 2 which is sealed at its lower end and has a wall that is transparent over the major portion of its length, a flexible hose 3 coupling the inside of the cup 1 to the inside of the cylinder 2, a cover 4 on the upper end of the cylinder 2 and a piston 5 having a piston rod 6 passing through a seal and valve 7 in the cover 4. A measuring scale 8 extends along the length of the wall of the cylinder 2. The cup 1 is lined with a flaccid, rubber membrane 10. A valve 11 provides access to a tube 12 which couples the hose 3 to the cylinder 2. It will be appreciated that there is an air-filled space within the region defined by the inner surfaces of the cup 1, the membrane 10, the hose 3, the tube 12, the cylinder 2 and the lower face of the piston 5, which is effectively closed, apart from the possibility of access via the valve 11.

In order to measure the volume of a human breast there are two possible methods of operation of the apparatus. In the first method of operation, the piston 5 is raised towards the cover 4 of the cylinder 2 by means of the rod 6, thereby tending to create a vacuum in the lower part of the cylinder 2 and to cause the rubber membrane 10 to be drawn into close contact with the inner wall of the cup 1. Since the elements define a closed region, it is found that, when the membrane 10 is tight against the inside of the cup 1 a position is reached at which the piston 5 cannot easily be moved further. The position of the piston at this point is then read off the scale 8. Let this value be volume A.

The cup 1 is then applied to the breast to be measured and the piston rod is moved downwards in order to tend to compress the air in the closed space of the system and displace the membrane 10 so that it is applied closely to the surface of the breast. The point at which the piston 5 cannot easily be moved further is then read-off the scale 8 from the same reference point on the piston 5 as before. Let this reading be volume B. The volume of the cup 1 is already known, it being X. The volume of the breast being measured can thus be computed by subtracting the value of volume B from the value of volume A and then subtracting the result from the value of volume X.

In a second method of operation, the piston 5 is pressed downwards by means of the rod 6 so that the piston 5 tends to compress the air in the closed system and the membrane 10 is caused to balloon outwards from the cup until a point of high resistance is reached. The volume at this point is read from the scale 8 on the cylinder 2. Let this volume be Y. The cup 1 is then applied firmly to the breast to be measured in such a way that the membrane 10 encases the breast. As a result the piston 5 is caused to move upwards to a point at which the reading on the scale 8 is Z. The measured volume of the breast is thus volume Z minus volume Y.

The valve 11 can be opened before the apparatus is used in order to adjust the amount of air in the closed system so that the piston 5 is at a convenient position in the cylinder 2.

It will be appreciated that variations and modifications can be made in the apparatus. For example, some other fluid than air could be used in the closed system. In the particular embodiment, the cylinder 2 is of glass. The cylinder could, of course, be made of some other material. Similarly, the cup 1, which is of a plastic material, could be of some other rigid material. In the particular embodiment, the piston 5 is a cylindrical block of polythene.

The piston 5 can be retained in the cylinder 2 at the position at which a measurement is to be taken in a simple manner by means, for example, of a locking device consisting of a flap-like disc of plastics material, which extends above the plate 7 at an angle of around 30° to the plate 7; the disc having a hole through which the rod 6 passes. In operation, the angle of the disc is adjusted by hand to allow the rod 6 to pass through the hole easily; the hole being such that, when the disc is allowed to settle to its normal angle, the rod 6 is gripped by the disc and held against further unwanted movement. Other means for temporarily locking the piston 5 in place can of course be used.

I claim:

1. Apparatus for use in estimating the volume of a human breast, comprising a cup having an inner surface and being adapted substantially to cover the breast, a flexible membrane coupled to said cup in a fluid-tight relation, the membrane defining, together with the inner surface of the cup, a variable volume space within the cup, a fluid container, means to vary the volume of fluid within the container, means for indicating changes in the volume of fluid within the container and means for coupling fluid within the container to the said space, whereby the membrane is firmly applied to the breast so that variations in volume of fluid in the said space result in corresponding variations in volume of fluid within the container to thus indicate the volume of said breast without fluid contacting said breast.

2. Apparatus as claimed in claim 1 including a flaccid rubber membrane constituting the flexible membrane and lining the cup.

3. Apparatus as claimed in claim 1 including a cylinder constituting the fluid container, and a piston within the cylinder, the piston providing the means for measuring the changes in volume.

4. Apparatus as claimed in any one of claims 1–3, wherein air constitutes the fluid.

5. A method of operation of the apparatus claimed in claim 1 wherein the volume of fluid in the space is reduced to a minimum, the corresponding first volume of fluid in the container is noted, the cup is applied to a breast, the volume of fluid in the container is varied until the membrane is applied closely to the breast, the corresponding second volume of fluid in the container is noted and the volume of the breast is computed by subtracting the second volume reading from the first volume reading and then subtracting the result from the known volume of the cup.

6. A method of operation of the apparatus claimed in claim 1, wherein the volume of fluid in the space is increased to a maximum, the corresponding first volume of fluid in the container is noted, the cup is applied to a breast until the membrane encases the breast, thereby reducing the volume of fluid in the space, the corresponding second volume of the fluid in the container is noted and the volume of the breast is computed by subtracting the first volume from the second volume.

* * * * *